US012551324B2

(12) United States Patent
Lamraoui et al.

(10) Patent No.: US 12,551,324 B2
(45) Date of Patent: Feb. 17, 2026

(54) OCCLUSIVE CUFF AND IMPLANTABLE OCCLUSIVE SYSTEM COMPRISING SUCH A CUFF

(71) Applicant: UROMEMS, Grenoble (FR)

(72) Inventors: Hamid Lamraoui, Grenoble (FR); Christopher Masri, Grenoble (FR)

(73) Assignee: UROMEMS, Grenoble (FR)

( * ) Notice: Subject to any disclaimer, the term of this patent is extended or adjusted under 35 U.S.C. 154(b) by 0 days.

(21) Appl. No.: 17/836,322

(22) Filed: Jun. 9, 2022

(65) Prior Publication Data

US 2022/0296349 A1 Sep. 22, 2022

Related U.S. Application Data

(63) Continuation of application No. 16/767,037, filed as application No. PCT/FR2018/052985 on Nov. 27, 2018, now abandoned.

(30) Foreign Application Priority Data

Nov. 28, 2017 (FR) ...................................... 1761287

(51) Int. Cl.
*A61F 2/00* (2006.01)

(52) U.S. Cl.
CPC .................................... *A61F 2/004* (2013.01)

(58) Field of Classification Search
CPC ........ A61F 2/004; A61F 5/0053; A61F 5/003; A61F 5/0066
See application file for complete search history.

(56) References Cited

U.S. PATENT DOCUMENTS 2,455,859 A 12/1948 Foley
3,744,063 A * 7/1973 McWhorter ............ A61F 2/004 128/DIG. 25

(Continued)

FOREIGN PATENT DOCUMENTS

CN 1636531 A 7/2005
EP 2815720 A1 12/2014

(Continued)

OTHER PUBLICATIONS

International Preliminary Report on Patentability received for PCT Patent Application No. PCT/FR2018/052985, mailed on Jun. 11, 2020, 14 pages (8 pages of English Translation and 6 pages of Original Document).

(Continued)

*Primary Examiner* — Samuel G Gilbert
(74) *Attorney, Agent, or Firm* — Thomas | Horstemeyer, LLC

(57) ABSTRACT

The invention relates to an occlusive cuff for selectively occluding an anatomical duct. The occlusive cuff has a band suited to surrounding an anatomical duct, provided with a closing device suited to maintaining the band wound upon itself over a determined length and an inflatable reservoir arranged on an inner face of the band. The cuff is characterised in that the inflatable reservoir extends over only a part of the length of the band, another part of the length defining a free inner surface of the band configured to form a bearing zone for the anatomical duct, such that when the band is maintained wound upon itself by the closing device, the inflatable reservoir is opposite said free inner surface of the band.

15 Claims, 3 Drawing Sheets

(56) References Cited

U.S. PATENT DOCUMENTS

| | | | | |
|---|---|---|---|---|
| 4,399,809 | A | 8/1983 | Baro et al. | |
| 4,428,365 | A | 1/1984 | Hakky | |
| 4,571,749 | A | 2/1986 | Fischell | |
| 4,584,990 | A * | 4/1986 | Haber | A61F 2/004 128/DIG. 25 |
| 4,592,339 | A | 6/1986 | Kuzmak et al. | |
| 4,632,114 | A * | 12/1986 | Todd | A61F 2/004 128/DIG. 25 |
| 4,803,985 | A | 2/1989 | Hill | |
| 4,828,544 | A * | 5/1989 | Lane | A61B 17/12 604/9 |
| 9,636,246 | B2 | 5/2017 | Frering | |
| 9,814,559 | B1 | 11/2017 | Forsell | |
| 10,350,044 | B2 | 7/2019 | Lamraoui | |
| 2004/0215054 | A1* | 10/2004 | Siegel | A61F 2/004 623/23.66 |
| 2004/0267288 | A1 | 12/2004 | Byrum et al. | |
| 2007/0156013 | A1 | 7/2007 | Birk | |
| 2007/0250086 | A1 | 10/2007 | Wiley et al. | |
| 2009/0270904 | A1 | 10/2009 | Birk et al. | |
| 2010/0217071 | A1* | 8/2010 | Ricol | A61F 5/0033 606/157 |
| 2015/0230904 | A1* | 8/2015 | Shabat | A61F 2/004 600/31 |
| 2017/0079760 | A1* | 3/2017 | Newman | A61F 2/004 |

FOREIGN PATENT DOCUMENTS

| | | | |
|---|---|---|---|
| JP | 2008296013 | A | 12/2008 |
| JP | 2009540964 | A5 | 11/2009 |
| JP | 2011518617 | A | 6/2011 |
| JP | 2014039854 | A | 3/2014 |
| WO | 2005009293 | A1 | 2/2005 |
| WO | 2009/048384 | A2 | 4/2009 |
| WO | 2013053929 | A1 | 4/2013 |
| WO | 2013101764 | A1 | 7/2013 |
| WO | 2013165563 | A1 | 11/2013 |
| WO | 2016083428 | A1 | 6/2016 |

OTHER PUBLICATIONS

International Search Report and Written Opinion received for PCT Patent Application No. PCT/FR2018/052985, mailed on Feb. 15, 2019, 18 pages (9 pages of English Translation and 9 pages of Original Document).

Preliminary Research Report received for French Application No. 1761287, mailed on Aug. 1, 2018, 3 pages (1page of French Translation Cover Sheet and 2 pages of original document).

* cited by examiner

OCCLUSIVE CUFF AND IMPLANTABLE OCCLUSIVE SYSTEM COMPRISING SUCH A CUFF

CROSS REFERENCE TO RELATED APPLICATIONS

This application is a continuation application of U.S. application Ser. No. 16/767,037, filed May 26, 2020, which application is a 35 U.S.C. § 371 national stage application of PCT Application No. PCT/FR2018/052985, filed Nov. 27, 2018, which application claims the benefit of French Application No. FR 1761287 filed Nov. 27, 2017, all of which are hereby incorporated by reference herein in their entireties.

FIELD OF THE INVENTION

The present invention relates to an occlusive cuff intended to selectively occlude an anatomical duct, such as a urethra or a bladder neck, as well as an implantable occlusive system comprising such a cuff.

PRIOR ART

Implantable occlusive systems exist intended to selectively occlude an anatomical duct, for example to remedy incontinence (case of artificial urinary or anal sphincters) or to limit intake of food into the stomach (case of gastric bands). The occlusion of the anatomical duct is brought about by the compression exerted by a cuff wound around said duct.

Among cuffs, the present text focuses on those based on fluid technology (the cuff comprising an inflatable reservoir coupled to a fluid circuit making it possible to fill or to empty selectively said reservoir, depending on the compression to exert on the anatomical duct).

Among occlusive systems, some are manual, that is to say that it is a user (for example the patient himself) who controls the compression applied by the cuff. Other systems are automatic, that is to say that they comprise one or more sensors, an actuator and a control unit for controlling the actuator to impose a determined compression of the anatomical duct by the cuff, without any intervention of a user being necessary.

The document WO 2016/083428 describes an automatic implantable occlusive system. This system comprises a fluid circuit comprising:

- an inflatable occlusive cuff containing a variable volume of fluid, intended to surround at least a part of a natural duct to occlude,
- a recipient of variable volume 41 filled with a fluid, said recipient comprising a fixed part 42 and a movable part 43,
- a fluid connection between the recipient and the occlusive cuff.

Furthermore, this system comprises an actuator mechanically coupled with the movable part of the recipient so as to displace said movable part linearly with respect to the fixed part to adjust the volume of the recipient.

The actuator and the recipient of variable volume are arranged in a leak tight housing containing a gas.

FIGS. 1A and 1B are views of an occlusive cuff 1' that can be used in this system, respectively in the free state (before implantation), and once implanted around the anatomical duct 2 to occlude.

Said cuff comprises a band 10 suited to surrounding said anatomical duct, and an inflatable reservoir 11' arranged on one face of the band 10, substantially over the entire length thereof. The inflatable reservoir 11 comprises at one of its ends a connector 12 making it possible to ensure a fluid connection between the inside of the reservoir 11 and a tubing 3 connected to the recipient.

At its end opposite to said connector 12, the band has an oblong opening 14, which is intended to be engaged on the connector 12 in order to maintain the cuff in position wound around the anatomical duct 2.

In the present text, "length" of the cuff is taken to mean the inner circumference of the cuff when said cuff is in its closed position. This length is noted Lio in FIG. 2A. Depending on the closing device of the cuff, this length is thus generally less than the total length of the band.

Cuffs of different lengths exist, depending on the targeted applications and patients.

The length of the occlusive cuff is chosen by the surgeon, as a function of the circumference of the anatomical duct at the location planned for the cuff.

In the case of artificial urinary sphincters, the cuff is generally implanted in women around the bladder neck, which has a large circumference. Typically, the length of the cuff for such an application is of the order to ten or so centimetres.

However, the use of a cuff of this dimension poses a certain number of problems for the implantation of the system and the operation thereof.

A first drawback of such a cuff is its bulkiness. Yet, the implantation of such a cuff around the bladder neck of women is awkward because there is little space around the bladder neck to insert the cuff. Moreover, the location of the cuff is very close to the vaginal wall, which the surgeon must take care not to perforate during the implantation.

On the one hand, the volume of the cuff being important, the fluid recipient must be dimensioned as a consequence to provide sufficient compression of the anatomical duct by the cuff. This implies an increase in the bulkiness of the housing containing said recipient.

Furthermore, the variation in volume of the recipient, which is implemented with a considerable amplitude, also leads to a reduction in the autonomy of the energy source which supplies the actuator, when said actuator is also arranged in the housing.

Consequently, the use of a cuff of large dimension implies at one and the same time great complexity of the implantation operation, an increase in the volume of the implantable housing and a decrease in the autonomy of the system.

DESCRIPTION OF THE INVENTION

An aim of the invention is thus to design an occlusive cuff that can be easily implanted around an anatomical duct having a large circumference, without causing the aforementioned problems.

To this end, the invention proposes an occlusive cuff for selectively occluding an anatomical duct, comprising:

- a band suited to surrounding said anatomical duct, provided with a closing device suited to maintaining the band wound upon itself over a determined length, and
- an inflatable reservoir arranged on an inner face of the band.

Said cuff is characterised in that the inflatable reservoir extends over only a part of the length of the band, another part of said length defining a free inner surface of the band configured to form a bearing zone for the anatomical duct, such that when the band is maintained wound upon itself by the closing device, the inflatable reservoir is opposite said free inner surface of the band.

In accordance with its common meaning, the term "free" signifies in the present text that the inner surface of the band does not support any additional element, which could be capable of being interposed between the band and the anatomical duct.

In the present text, the term "inner" designates the face of the cuff which, when the cuff is in closed position, is intended to come into direct contact with the anatomical duct. The term "outer" designates the opposite face.

In a particularly advantageous manner, the length of the reservoir is chosen such that when the band is wound upon itself around the anatomical duct and when the reservoir is inflated, the anatomical duct is compressed between the wall of the reservoir and the free surface of the band, the reservoir exerting a push force of the anatomical duct against said free surface of the band.

The inflatable reservoir preferably extends over a length less than or equal to 75% of the length of the band.

The length of the band may be comprised between 30 and 110 mm, preferably between 70 and 110 mm.

According to an embodiment, the band is formed of a textile coated with a biocompatible elastomer. The inflatable reservoir may be made of a biocompatible elastomer. According to an embodiment, said biocompatible elastomer is silicone.

Advantageously, the cuff further comprises a connector arranged at one end of the band to ensure a fluid connection between the reservoir and a tubing.

According to an embodiment, the closing device comprises an opening formed at one end of the band and able to engage around the connector to maintain the band wound upon itself.

Alternatively, the closing device comprises a surface provided with teeth at one end of the band and an attachment device comprising a slot for the insertion of said end, configured to block the teeth against an extraction force of said end. Preferably, these teeth are arranged on the outer face of the band.

The invention also relates to an implantable occlusive system comprising a cuff such as described above and an implantable housing comprising a pump in fluid connection with the cuff to vary the volume of fluid in the inflatable reservoir.

According to a particular application of the invention, the occlusive system is an artificial urinary sphincter.

DESCRIPTION OF THE FIGURES

Other characteristics and advantages of the invention will become clear from the detailed description that follows, with reference to the appended drawings among which.

Figure 1A:
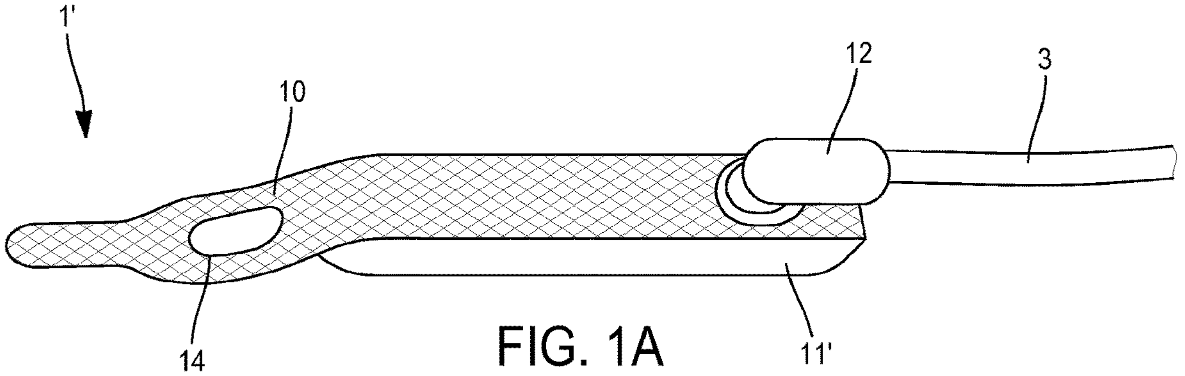
FIG. 1A is a schematic view of an occlusive cuff of known type, such as supplied to the surgeon with a view to implantation.

Identical reference signs from one figure to the other designate elements that are identical or at least fulfil the same function.

DETAILED DESCRIPTION OF EMBODIMENTS OF THE INVENTION

Compared to known occlusive cuffs, the invention proposes reducing the length of the inflatable reservoir.

FIGS. 2A-20 schematically illustrate a cuff 1 according to an embodiment of the invention, respectively in the free state, in the closed state without exerting compression on the duct and in a configuration of occlusion of said duct.

The inflatable reservoir 11 extends over less than 75% of the length Lio of the band, preferably less than 60% of the length of the band, and in an even more preferred manner less than 50% of the length of the band. The length of the inflatable reservoir is noted Lit.

Thus, for example, for a cuff 10 cm long, the length of the inflatable reservoir is 4.5 cm.

In other words, the inner face of the band 10 is broken down into a region of length Lit on which is arranged the reservoir 11, and a region of length $L_{13}$ which forms a free surface, that is to say devoid of reservoir, and which constitutes a bearing zone for the anatomical duct.

When the cuff is in closed position, the wall of the reservoir 11 thus lies facing the free surface 13 of the band (the anatomical duct 2 being interposed between these two surfaces, as shown in FIG. 28).

Figure 1B:
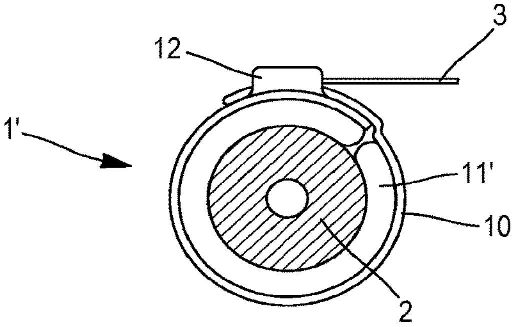
FIG. 1B is a schematic view of the cuff of FIG. 1A, after implantation around the anatomical duct (represented as not exerting any compression on said duct)

To the contrary, in a cuff of known type such as represented in FIGS. 1A and 1B, the two ends of the reservoir are flush when the cuff is closed. Even if a slight play may subsist between these two ends, notably to take account of the variation in volume of the reservoir when it is inflated, the corresponding zone of the band does not constitute a bearing zone for the anatomical duct.

Returning to the invention, when the reservoir 11 is inflated, it pushes the anatomical duct against the free surface 13 of the band, thus progressively occluding the duct (cf. FIG. 20). Thus, the anatomical duct is compressed between, on the one hand, the reservoir 11 and, on the other hand, the free surface 13.

Advantageously, a panoply of cuffs of different lengths is made available to the surgeon, from which the surgeon will chose the most suitable for the patient and for the location planned for the implantation. In this panoply, the length of the band is generally comprised between 3 and 11 cm.

For cuffs of small length (that is to say typically less than 7 cm), the inflatable reservoir may be arranged over the entire length of the cuff.

From a certain length of cuff (for example 7 cm), the length of the inflatable reservoir may be fixed (for example of the order of 4.5 cm). Thus, it is possible to use the same pump for all cuff dimensions, which avoids multiplying the housing references.

Such a cuff may be manufactured in the following manner.

On the one hand, the band is formed of a textile coated with a biocompatible elastomer. Advantageously, the textile is a biocompatible polyester fabric, known notably by the name of DACRON™ and the elastomer is silicone. The band may be cut, for example by water jet, from a sheet of large dimensions. The band thus formed has the advantage of being smooth, of not setting into the anatomical tissues (thus allowing potential explantation of the cuff) and of not being stretchable.

On the other hand, the reservoir is made of a biocompatible elastomer, for example silicone, preferably by dipping so as to ensure a perfectly smooth surface state in order to ensure a flexible contact with the anatomical duct.

The reservoir is bonded onto the band.

The connector is for its part moulded and bonded onto the face of the band opposite to the reservoir while passing through said band to ensure a fluid connection between the reservoir and the tubing which is sleeved on the connector.

Figure 2A:
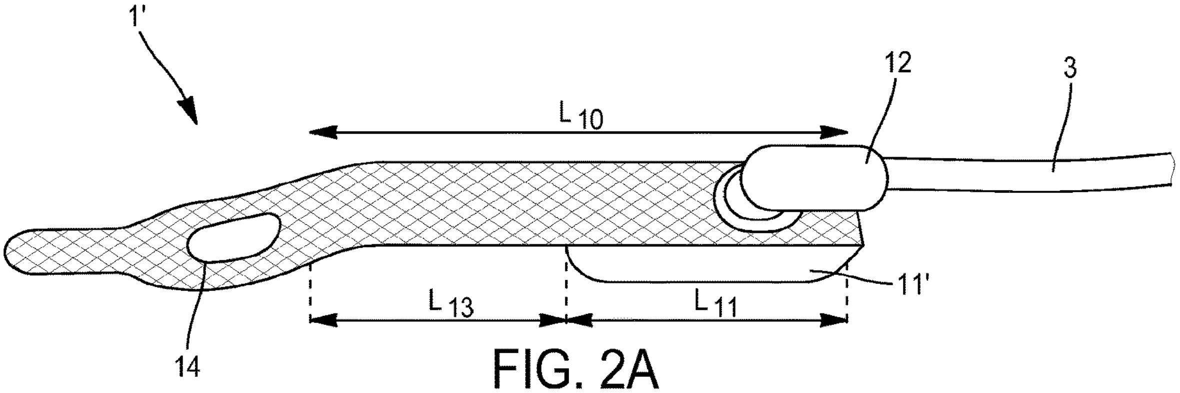
FIG. 2A is a schematic view of an occlusive cuff according to an embodiment of the invention, such as supplied to the surgeon with a view to implantation.
Figure 2B:
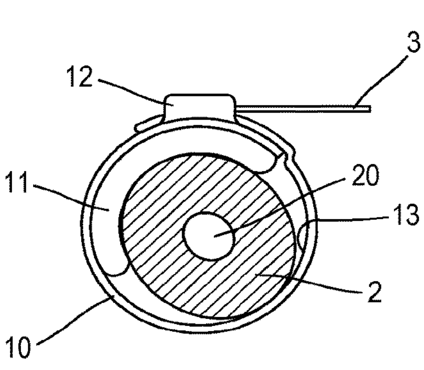
FIG. 2B a schematic view of the cuff of FIG. 2A, after implantation around the anatomical duct (represented as not exerting any compression on said duct)
Figure 2C:
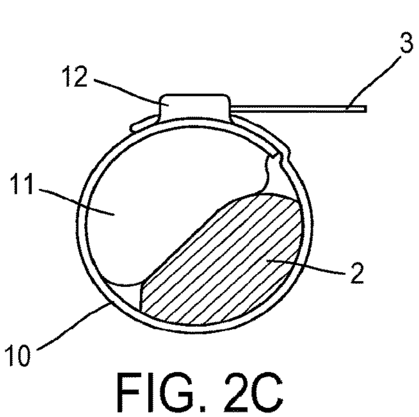
FIG. 2C is a schematic view of the cuff of FIG. 2A, after implantation around the anatomical duct, in configuration of obturation of said duct.

According to an embodiment, illustrated in FIG. 2A, the closing device of the cuff 1 comprises an oblong opening 14 intended to engage on the connector 12.

Figure 3:
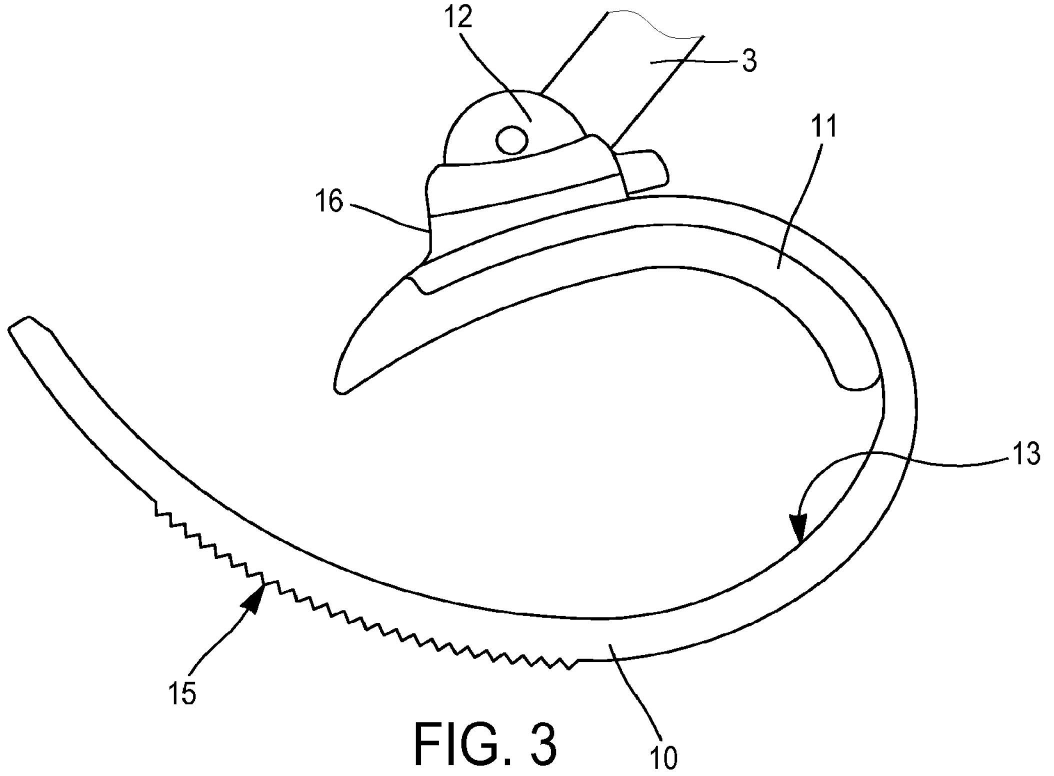
FIG. 3 illustrates an alternative of the system for closing the occlusive cuff.

According to another embodiment, illustrated in FIG. 3, the band has at a first end a plurality of teeth 15 and at its other end, preferably at the level of the connector 12, an attachment device 16 comprising a slot suited to enabling the insertion of the first end and provided with a retaining system only allowing a displacement of the band 10 in the direction of the insertion (the teeth opposing a traction movement aiming to make the band come out of the slot). Advantageously, the teeth 15 lie on the outer face of the band 10, in order not to risk eroding the compressed part of the duct. The teeth may form an integral part of the band or be manufactured by moulding then bonded onto the band.

Naturally, those skilled in the art could choose any other closing device without however going beyond the scope of the present invention.

The reduction in the length of the inflatable reservoir has three main advantageous effects.

A first effect is a decrease in the bulkiness of the cuff, which facilitates its implantation in zones where the available space is limited. In the deflated state prior to implantation, the cuff is in the form of a band having a small thickness, which can thus be inserted relatively easily into the zone dissected around the bladder neck, unlike the cuff described in the document WO 2013/165563, which uses the cooperation of an anvil integral with the inner surface of the band and a hammer integral with the reservoir to compress the anatomical duct. The anvil and hammer being relatively rigid, they have a non-negligible bulkiness in the implantation zone. Conversely, in the present invention, as is clearly shown in FIGS. 2B and 2C, when the cuff is implanted around the anatomical duct, said duct is in direct contact with the reservoir 11 and with the free surface 13 of the band which are flexible parts, which makes it possible to minimise the thickness of the cuff and reduce the risk of erosion of body tissues.

A second advantageous effect of the invention is a reduction in the volume of fluid necessary to swell the reservoir in order to occlude the anatomical duct.

Consequently, the volume of the recipient of variable volume contained in the housing remains limited, and the autonomy of the energy source is not penalised.

A third effect is a modification of the mode of action of the cuff on the anatomical duct.

Figure 4A:
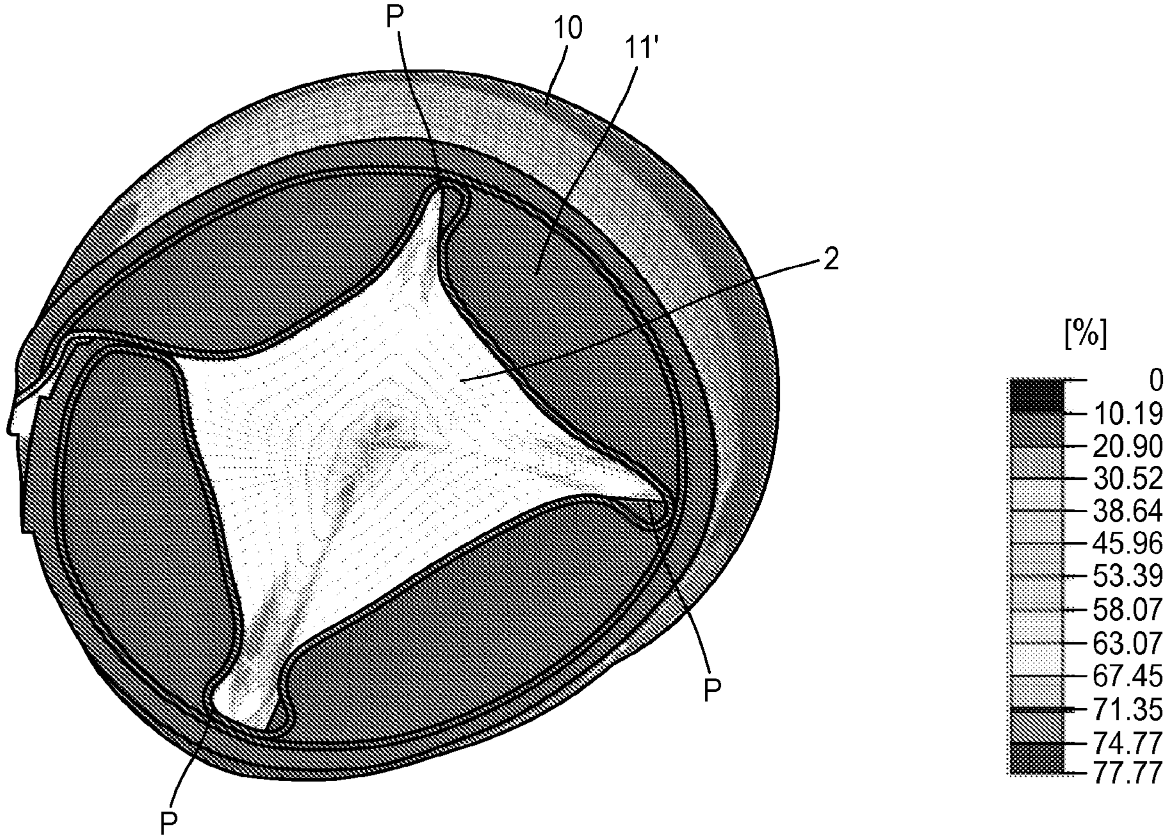
FIG. 4A illustrates a simulation by finite elements of the compressive stress generated in a bladder neck by the compression exerted by a cuff such as illustrated in FIG. 1A.

FIG. 4A shows the result of a simulation by finite elements of the compressive stresses applied to the bladder neck by a cuff according to the prior art, such as illustrated in FIG. 1A, for a fluid pressure in the cuff of 120 cm $H_2O$. It may be observed that the curvature of the cuff combined with a swelling of the reservoir has the effect of dividing the reservoir 11' into four pockets which each extend over around one quarter of the inner circumference of the cuff. Yet, the bladder neck is pinched between two adjacent pockets, and is subjected, in these pinch zones P, to local mechanical stresses well above the stresses to which the remainder of the neck is subjected. These localised stresses are liable to damage the bladder neck, for example atrophying it.

Figure 4B:
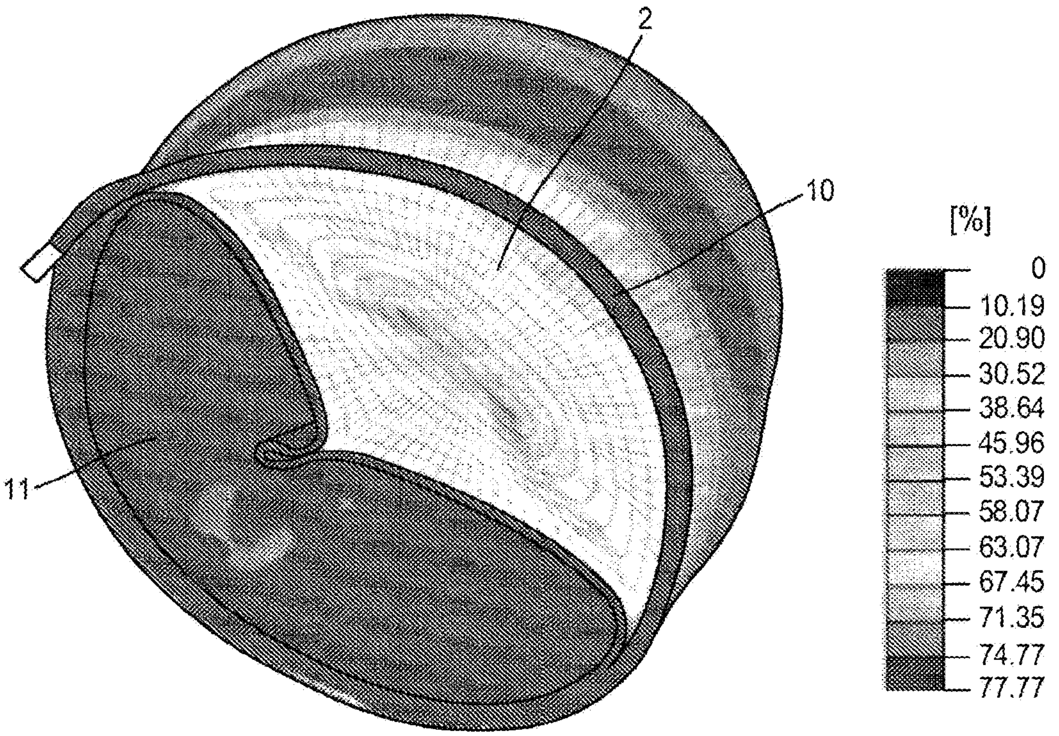
FIG. 4B illustrates a simulation by finite elements of the compressive stress generated in the bladder neck by the compression exerted by a cuff according to an embodiment of the invention.

In FIGS. 4A and 4B, the stress levels represented by dark colours correspond to high stresses on the colour scale shown on the right of each simulation.

FIG. 4B shows the result of a simulation by finite elements of the compressive stresses applied to the bladder neck by a cuff according to an embodiment of the invention, such as illustrated in FIG. 2A, for a fluid pressure in the cuff of 120 cm $H_2O$. It may be observed that the reduction in the length of the inflatable reservoir 11 has the effect of eliminating the pinch zones of the bladder neck, and consequently eliminating the excess stresses undergone locally by the bladder neck. The bladder neck is thus less likely to be damaged.

Figure 5:
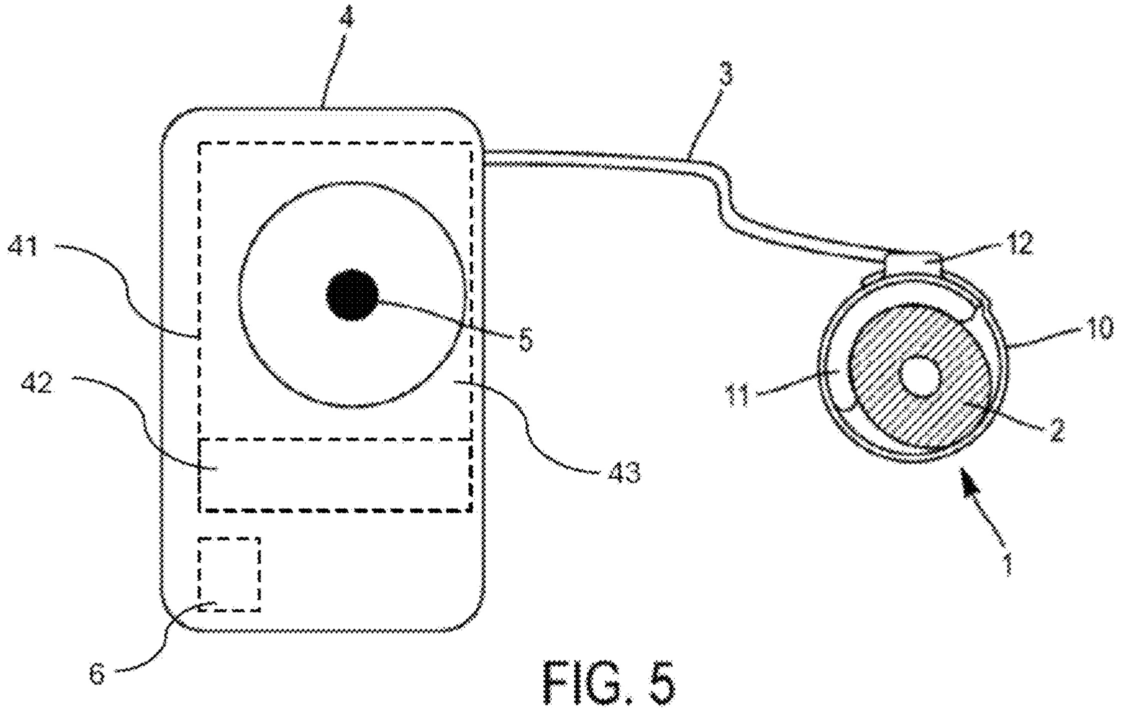
FIG. 5 illustrates an implantable occlusive system comprising a cuff according to an embodiment of the invention.

FIG. 5 illustrates an implantable occlusive system comprising an implantable housing comprising a pump, and an occlusive cuff such as described above, in fluid connection with the pump. The pump is advantageously one of the devices described in the document WO 2016/083428.

The housing 4 contains the recipient of variable volume, the actuator 6 as well as said electronic module(s) and, if need be, the energy source. The housing contains a gas, for example air. Said housing must be leak tight to avoid any transfer of fluid or gas from or to the intracorporal medium. The housing is made of a biocompatible material and may for example be made of implantable titanium and sealed by laser welding. A control of the leak tightness may notably be carried out with helium (for example, leakage rate less than $10^{-9}$ mbar·l/s of helium) to ensure the total leak tightness of the housing for the period for which the system is implanted.

The recipient of variable volume is connected to the cuff 1 by the tubing 3.

Advantageously, the housing comprises, in a wall delimiting the recipient of variable volume, a puncture port 6 perforable by a needle and able to close in a leak tight manner after removal of the needle, making it possible to inject or to remove fluid from the recipient.

The invention claimed is:

1. A method for selectively occluding an anatomical duct, comprising:

providing a band comprising a closing device and an unstretched inflatable reservoir on an inner face of the band, and an implantable housing containing a gas, a fluid recipient of variable volume and a pump, said pump comprising an actuator configured for adjusting the volume of the inflatable reservoir and an electronic module configured to control said actuator, and wherein the band is remote from the implantable housing, said inflatable reservoir being in fluid connection with the pump to selectively increase or decrease the volume of fluid in the inflatable reservoir, said inflatable reservoir extending over only a first part of a length of the band, a second part of said length defining a free inner surface of the band, winding the band around the anatomical duct so that the first part of the length of the band less than or equal to 75% of a length of the band in wound position and a first portion of the anatomical duct is supported by the free inner surface of the band, and a second portion of the anatomical duct opposite to the first portion is in contact with the inflatable reservoir, locking the closing device to maintain the band wound upon itself; and inflating the reservoir so as to compress the anatomical duct between the inflated reservoir and the free inner surface of the band.

2. The method of claim 1, wherein the anatomical duct is in direct contact with the free inner surface of the band.

3. The method of claim 1, wherein the anatomical duct is a urethra or a bladder neck.

4. The method of claim 1, wherein the first part of the length of the band is less than or equal to 60% of the length of the band in wound position.

5. The method of claim 4, wherein the first part of a determined length of the band is less than or equal to 50% of the length of the band in wound position.

6. The method of claim 1, wherein a length of the band in wound position is comprised between 30 and 110 mm.

7. The method of claim 1, wherein the band is formed of a textile coated with a biocompatible elastomer.

8. The method of claim 1, wherein the reservoir is made of a biocompatible elastomer.

9. The method of claim 8, wherein said biocompatible elastomer is silicone.

10. The method or claim 1, further comprising arranging a connector at a first end of the band to ensure a fluid connection between the reservoir and a tubing.

11. The method of claim 10, wherein the locking step comprises engaging an opening formed at a second end of the band opposite to the first end around the connector.

12. The method of claim 1, wherein the locking step comprises inserting an end of the band provided with teeth on a surface into a slot provided on the attachment device, hereby blocking the teeth against extraction force of said end.

13. The method of claim 12, wherein the teeth are arranged on an outer face of the band.

14. A method for minimizing local mechanical stresses applied on tissue surrounding an anatomical duct during selective occlusion thereof, comprising:

providing a band comprising a closing device and an unstretched inflatable reservoir arranged on only a part of an inner face of the band, and an implantable housing containing a gas, a fluid recipient of variable volume and a pump comprising an actuator configured for adjusting the volume of the inflatable reservoir and an electronic module configured to control said actuator, wherein the band is remote from the implantable housing, said inflatable reservoir being in fluid connection with the pump to selectively increase or decrease the volume of fluid in the inflatable reservoir, winding the band around the anatomical duct so that a first part of a length of the band less than or equal to 75% of a length of the band in wound position and a first portion of the anatomical duct is in contact with the inflatable reservoir and a second portion of the anatomical duct is in contact with a free inner surface of the band, locking the closing device to maintain the band wound upon itself;

inflating the reservoir so as to compress the anatomical duct between the inflated reservoir and the free inner surface of the band, a length of the inflatable reservoir being chosen to eliminate pinch zones subject to local mechanical stresses in the anatomical duct.

15. A method for selectively occluding an anatomical duct, comprising:

providing a band comprising a closing device and an unstretched inflatable reservoir on an inner face of the band, and an implantable housing containing a gas, a fluid recipient comprising a fixed part and a movable part, an actuator mechanically coupled with the movable part to displace said movable part linearly with respect to the fixed part to selectively increase or decrease a volume of the fluid in the recipient and an electronic module configured to control said actuator, wherein the band is remote from the implantable housing, the inflatable reservoir being connected to the fluid recipient by a tubing to transfer fluid between the fluid recipient and the inflatable reservoir upon displacement of the movable part of the fluid recipient, said inflatable reservoir extending over only a first part of a length of the band, a second part of said length defining a free inner surface of the band, winding the band around the anatomical duct so that the first part of the length of the band less than or equal to 75% of a length of the band in wound position and a first portion of the anatomical duct is supported by the free inner surface of the band, and a second portion of the anatomical duct opposite to the first portion is in contact with the inflatable reservoir, locking the closing device to maintain the band wound upon itself; and controlling the actuator to inflate the reservoir so as to compress the anatomical duct between the inflated reservoir and the free inner surface of the band.

* * * * *